United States Patent [19]

Pekar et al.

[11] Patent Number: 5,437,615
[45] Date of Patent: Aug. 1, 1995

[54] INFLATABLE SUPPORT DEVICE

[75] Inventors: Robert W. Pekar, Florence; Paul E. Litchfield, Cerafton; Steven F. Smith, Taunton; Stephen J. Cardillo, Everett, all of Mass.

[73] Assignee: Reebok International Ltd., Stoughton, Mass.

[21] Appl. No.: 137,792

[22] Filed: Oct. 19, 1993

[51] Int. Cl.⁶ ............................................. A61F 5/00
[52] U.S. Cl. ...................................... 602/19; 602/13
[58] Field of Search ..................... 128/876, DIG. 20; 602/5, 13, 19, 23, 26, 27; 601/148, 149, 151, 152; 2/338, 311, 312, 267; 450/38; 441/106, 108, 113

[56] References Cited

U.S. PATENT DOCUMENTS

| | | |
|---|---|---|
| 1,646,590 | 10/1927 | Mildenberg . |
| 1,970,802 | 8/1934 | Johnson . |
| 2,760,212 | 8/1956 | Gazelle . |
| 4,135,503 | 1/1979 | Romano . |
| 4,178,922 | 12/1979 | Curlee . |
| 4,178,923 | 12/1979 | Curlee . |
| 4,348,774 | 9/1982 | Woodson . |
| 4,552,135 | 11/1985 | Racz et al. . |
| 4,622,957 | 11/1986 | Curlee . |
| 4,682,587 | 7/1987 | Curlee . |
| 4,682,588 | 7/1987 | Curlee . |
| 4,703,750 | 11/1987 | Sebastian et al. . |
| 4,756,306 | 7/1988 | Curlee . |
| 4,789,202 | 12/1988 | Alter . |
| 4,836,194 | 6/1989 | Sebastian et al. . |
| 4,905,993 | 3/1990 | Barone . |
| 4,968,027 | 11/1990 | Anderson . |
| 4,993,409 | 2/1991 | Grim . |
| 5,022,109 | 6/1991 | Pekar . |
| 5,062,414 | 11/1991 | Grim . |
| 5,088,478 | 2/1992 | Grim .................................. 602/27 |
| 5,113,599 | 5/1992 | Cohen et al. ......................... 36/88 |
| 5,152,302 | 10/1992 | Fareed ............................. 602/13 X |
| 5,195,948 | 3/1993 | Hill et al. . |

FOREIGN PATENT DOCUMENTS

0479014A1   4/1992   European Pat. Off. .

OTHER PUBLICATIONS

Custom Back Support Advertisement, *Life Magazine* Jul. 1993, p. 77.
Grolen, Back and Wrist Supports W3 Advertisement, Items A, B and C, Source Unknown.

*Primary Examiner*—Linda C. M. Dvorak
*Attorney, Agent, or Firm*—Sterne, Kessler, Goldstein & Fox

[57] ABSTRACT

A support is disclosed comprising a belt which encircles a wearer's waist. The belt which is inflatable has an on-board inflation pump and may be used for weight lifting. The inflatable weight lifting belt includes a bladder defined by a single chamber having inflation and deflation mechanisms which allow the wearer to selectively adjust the amount of air in the bladder. The bladder has an oblong portion which is positioned on the belt so that when the belt is worn, the oblong portion is positioned adjacent to the wearer's lower back for support. An elongated portion of the bladder extending through the aperture of the belt is integrally formed with inflation and deflation mechanisms on the other side of the belt. In the preferred embodiment, the inflation mechanism comprises a pump and a one-way valve and the deflation mechanism comprises an exhaust valve.

20 Claims, 4 Drawing Sheets

INFLATABLE SUPPORT DEVICE

BACKGROUND OF THE INVENTION

1. Field of the Invention

The present invention relates generally to support devices for the human body and more particularly to an improved inflatable belt worn during the lifting of heavy objects such as weights.

2. Related Art

Those who lift heavy objects, for instance, weight lifters, often use belts to help support their spine and back muscles while lifting such objects. The belts commonly employed attempt to provide specific support to the lumbar area of the spine. However, inherent difficulties arise due to the materials from which such belts are manufactured. The belts are usually made from a thick strip of stiff leather. Although leather provides firm support, its inflexibility prevents it from providing uniform surface contact with the lumbar area of the spine. As a result, belts made entirely from leather do not provide uniform support to the curved spinal areas of the back, and particularly the lumbar or arch region of the back.

An example of a conventional weight lifting belt is shown in FIG. 2 of U.S. Pat. No. 4,348,774 to Woodson. In this belt, the central portion is enlarged in comparison to the end portions of the belt to provide a wider base of support to the spinal region of a wearer. The Woodson patent describes the addition of a thin layer of foamed, flexible plastic on the inner surface of the belt to protect the wearer against chafing. Because the liner is thin and has uniform thickness, the amount of support which the liner provides to the lumbar area of the spine is dependent upon how tightly the wearer cinches the belt about his or her waist. However, even if the belt is pulled as tightly as possible, the thin, foamed layer still may not completely support a particular wearer's spine due to the dimensional variations that are possible in the curvature of the lumbar region of the body.

Thus, further development in the technology has been directed toward providing specific support in the lumbar spinal region of the back. For example, U.S. Pat. No. 4,905,993 to Barone describes a weight lifting belt designed to provide direct localized support of the lower spine by providing a narrow pad constructed of high density foam shaped to fit into the "indentation" of the spine. However, the narrow width and the fixed shape of the pad could actually create an area of concentrated pressure against the spine so localized as to be uncomfortable.

Accordingly, attempts have been made to provide improved lumbar support while accommodating the variations in the profile of the human lumbar spinal region. At least one has attempted to provide customized lumbar support by replacing the fixed-shape pad with a centrally-located fluid-filled pad. For example, U.S. Pat. No. 4,968,027 to Anderson describes a weight lifting belt having a lumbar support in the form of a moldable gel. While the gel does conform to fit, in part, the lumbar region of a user's back, the fluid-filled pad is of constant volume. A constant-volume pad is still unable to provide variable support to the lumbar spinal region independent of tightly cinching the belt about the user's waist.

Others have tried to use an adjustable-volume fluid-filled bladder; for example, U.S. Pat. No. 4,552,135 to Racz et al. describes a support belt having a centrally-located pad including a chamber filled with open-cell sponge-like material. A valve connects the chamber with the atmosphere and controls the flow of air into and out of the chamber. The valve provides the advantage that the chamber is adjustable to fit an individual's spinal curvature. However, due to loss of air pressure in the chamber from unavoidable diffusion resulting from use, the belt must be removed from the body in order to reinflate the chamber. This is because air is drawn into the chamber only when the sponge-like material forces the walls of the chamber apart which occurs only by relieving the compression forces exerted by the wearer's body on the chamber. Thus, the wearer must repeatedly take off the belt to reinflate as pressure is lost during use.

Therefore, others have attempted to provide a belt that is inflatable while the belt is worn to satisfy the dual goals of providing a support device capable of being adjusted even after the belt is worn as well as providing a support device which can accommodate for the dimensional variation in the curvature of the lumbar region of the human body.

For example, U.S. Pat. No. 1,646,590 to Mildenberg; U.S. Pat. No. 4,178,923 to Curlee; U.S. Pat. No. 4,703,750 to Sebastian et al.; and U.S. Pat. Nos. 4,993,409 and 5,062,414 to Grim all describe associated mechanisms for inflating belts with bladders. Some, such as the Mildenberg patent provide for the bladder to be pressurized by the wearer's blowing into a conduit attached to the bladder. Not surprisingly, the wearer's act of tightening and expanding the muscles of the diaphragm of the body to pressurize the bladder could make blowing air into the bladder more difficult.

Others describe inflation mechanisms such as mechanical pumps which are removably attached to the associated belt. Not only is this arrangement inconvenient in that it requires that the user have the separate pump nearby during use to quickly accommodate for diffusion, but it also requires the provision of at least one conduit to communicate fluid between the pump and the bladder, which adds to the manufacturing costs and propensity for fluid leakage.

Others, such as U.S. Pat. No. 4,135,503 to Romano; U.S. Pat. Nos. 4,178,922; 4,622,957; 4,682,588; and 4,756,306 to Curlee; U.S. Pat. No. 4,836,194 to Sebastian et al., and U.S. Pat. No. 5,195,948 to Hill et al. all describe belts which incorporate an inflation mechanism permanently attached to the belt. While this arrangement does eliminate the inconvenience of having to have a separate inflation mechanism handy when using the belt, all of these patents still require the use of a separate conduit between the pump and the bladder.

Further, several of these patents also describe bladders having multiple pneumatic chambers and bladders having complex geometrical profiles. A bladder having multiple pneumatic chambers provides less ultimate volume than a bladder having the identical profile with a single pneumatic chamber. A single pneumatic chamber having greater ultimate volume has enhanced potential for providing customized fit.

Multiple pneumatic chambers also require additional tooling expense in manufacturing as does a bladder having a complex geometrical profile.

Thus, the need exists for a belt which provides lumbar support, but avoids the "localized pressure effect," which is capable of being adjusted independent of tightly cinching a belt about a wearer's waist, which can accommodate the wide variation in the dimensions of the lumbar spinal region of the human body, which does not require a separate conduit for communication between an inflation device and a bladder, which has an inflation device fixed on the belt, which has a bladder constructed to have a single chamber, which has a bladder with a simple geometry, and which may be constructed with a minimum of manufacturing cost.

SUMMARY OF THE INVENTION

The present invention is a support comprising an inflatable weight lifting belt with an on-board inflation pump. The belt is designed to fit substantially around the wearer's waist.

The inflatable weight lifting belt includes a bladder defined by a single chamber having inflation and deflation means. The bladder avoids the provision of a separate conduit between the inflation means and the bladder.

The bladder has an oblong portion which is positioned on the belt so that when the belt is worn, the oblong portion is positioned adjacent to the wearer's lower back. The oblong portion directly supports the wearer's back. An elongated portion of the bladder disposed on the other side of the belt is integrally formed with inflation and deflation means. In the preferred embodiment, the inflation means comprises an inflation mechanism or pump and a one-way valve. The deflation means comprises an exhaust valve.

The above and other objects and advantages of this invention will be more readily apparent from a reading of the following description of an exemplary embodiment thereof taken in conjunction with the following drawings.

BRIEF DESCRIPTION OF THE FIGURES

The accompanying drawings, which are incorporated in and form a part of the specification, illustrate an embodiment of the present invention and, together with the description, serve to explain the principles of the invention.

In the drawings.

DETAILED DESCRIPTION OF THE PREFERRED EMBODIMENT

Figure 1:
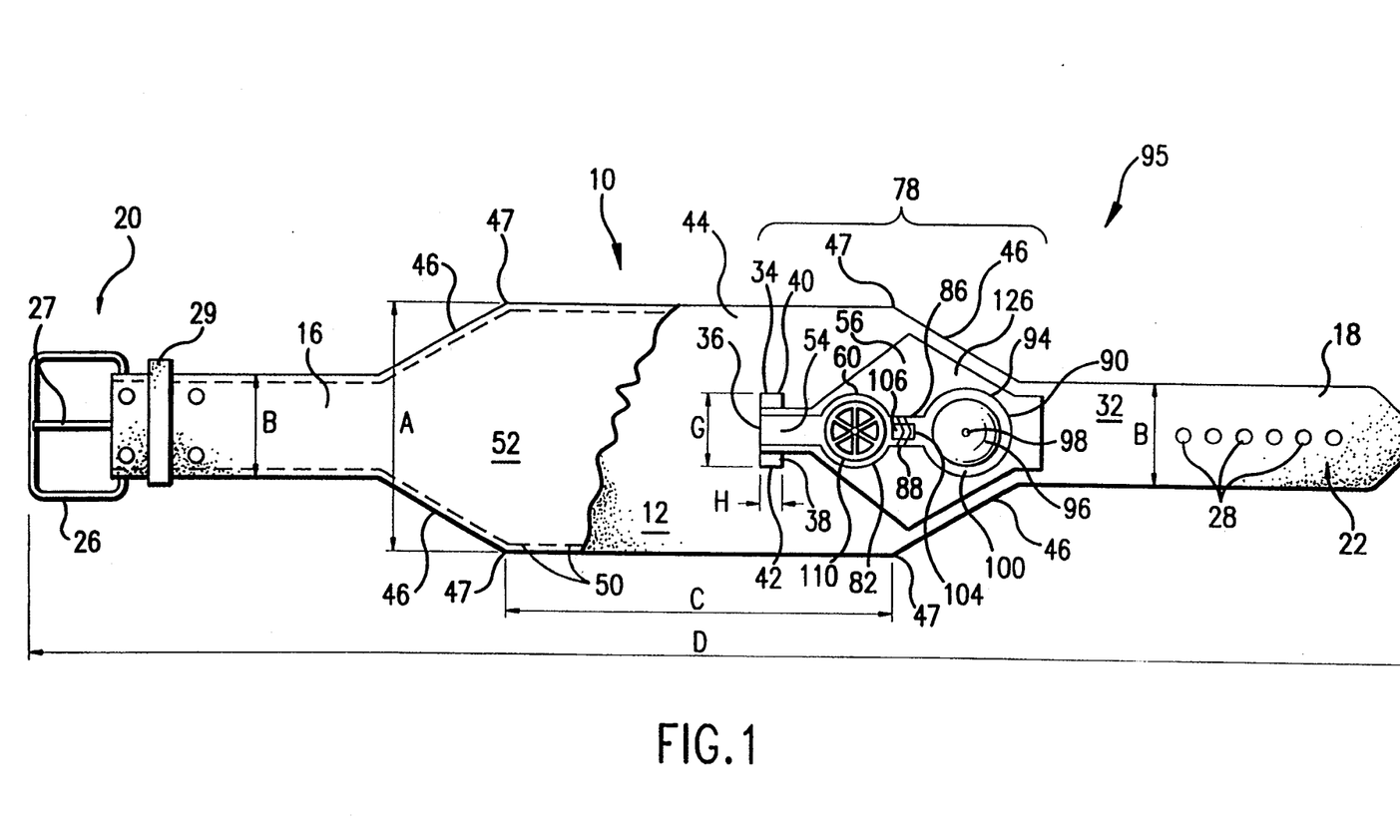
FIG. 1 is a partial cutaway plan view of one side of an article of manufacture according to the present invention.

Referring to the accompanying drawings, wherein like numbers indicate like elements, in FIG. 1 an adjustable support is shown generally at 10. Support 10 comprises a belt 12, a bladder 54, and an inflation/deflation mechanism shown generally at 95. Each of these elements will now be described in greater detail.

Belt 12 is generally elongated in shape and is comprised of a generally rectangular central portion 44 and generally rectangular ends 16 and 18. Central portion 44 has a central width A. Ends 16 and 18 are equal in width B. Central width A is wider than end width B of belt 12 to provide a wider base of support to the spinal region of a wearer. In the preferred embodiment, central width A is approximately 4 inches wide, while end width B is approximately 2½ inches. Four tapered portions 46 provide a transition between width A of central portion 44 and width B of ends 16 and 18. Specifically, at four juncture points 47, width A of central portion 44 begins to taper to width B of ends 16 and 18.

The length of central portion 44 is designated by C. In the preferred embodiment, length C is approximately 16¼ inches. Ends 16 and 18 are approximately 9¾ and 17 inches long, respectively, from juncture points 47 to their respective distal ends.

Belt 12 has an overall length D measured from the distal point of end 16 to the distal point of end 18. Belt 12 may be manufactured in a variety of different lengths in order to fit a variety of different wearers' waists. In the preferred embodiment, length D is approximately 43 inches. Throughout this description, the actual measurements for the preferred embodiment are measured with reference to a size "medium" belt. However, other embodiments are anticipated having belt sizes such as "small" and "large." Accordingly, the various measurements provided may be altered proportionately to accommodate differently sized belts.

A cooperating fastener shown generally at 20 and 22 is disposed on ends 16 and 18, respectively, of belt 12. Cooperating fastener 20, 22 removably fastens ends 16 and 18 about the body of a wearer. The preferred embodiment utilizes a conventional buckle 26 and pin 27 which are disposed on end 16 of belt 12. Eight pin-receiving apertures 28 are disposed on end 18 of belt 12. In use, belt 12 is wrapped about the waist of a wearer. End 18 is inserted through buckle 26. Pin 27 is inserted through one of apertures 28. End 18 is then slipped through a retaining loop 29 also disposed on end 16.

Other means suitable for releasably fastening together ends 16 and 18 of belt 12, such as hook-and-pile fasteners, snaps, strapping rings and button-and-loop may alternatively be used.

Figure 2:
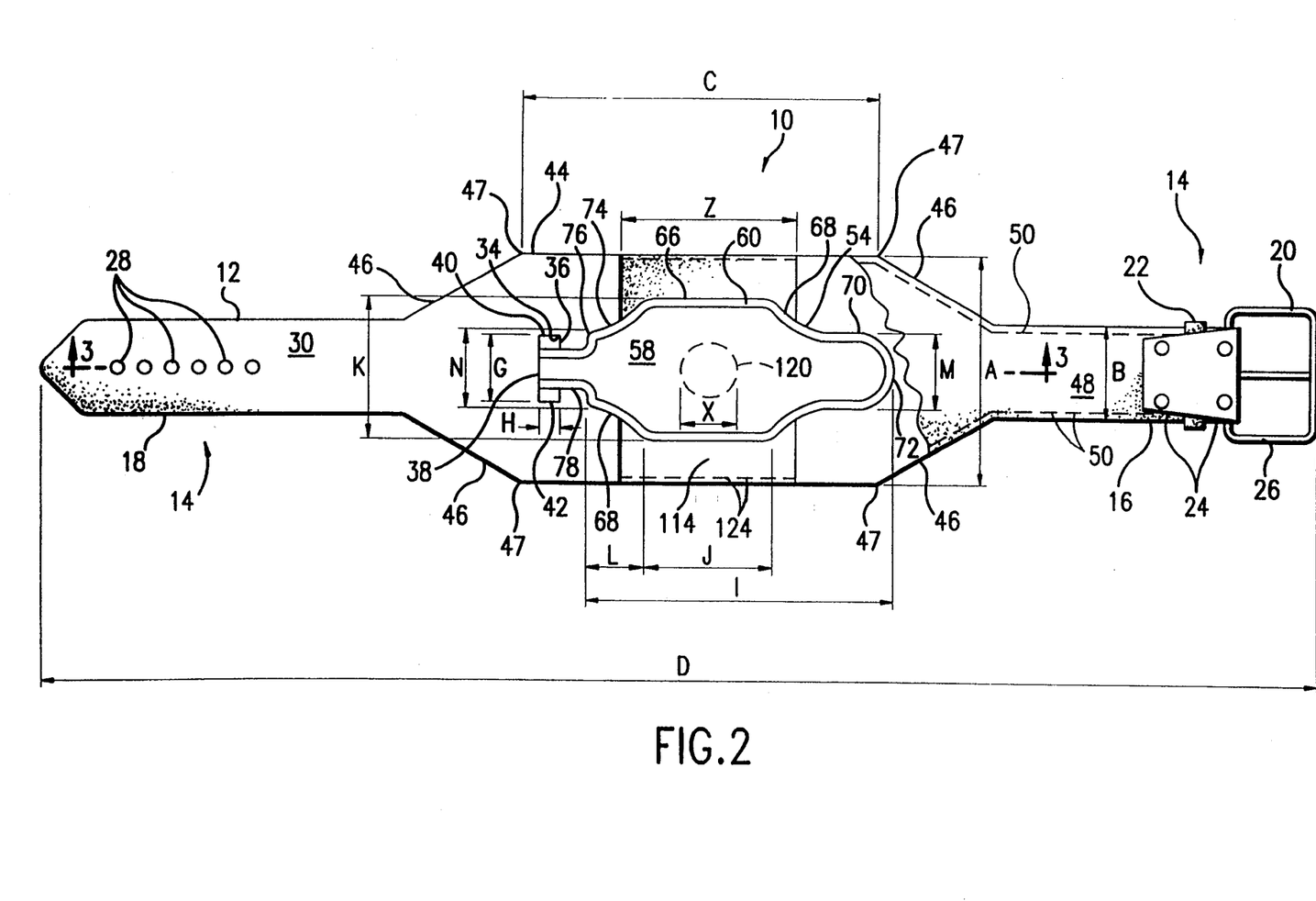
FIG. 2 is a partial cutaway plan view of the other side of the article of manufacture shown in FIG. 1.
Figure 3:
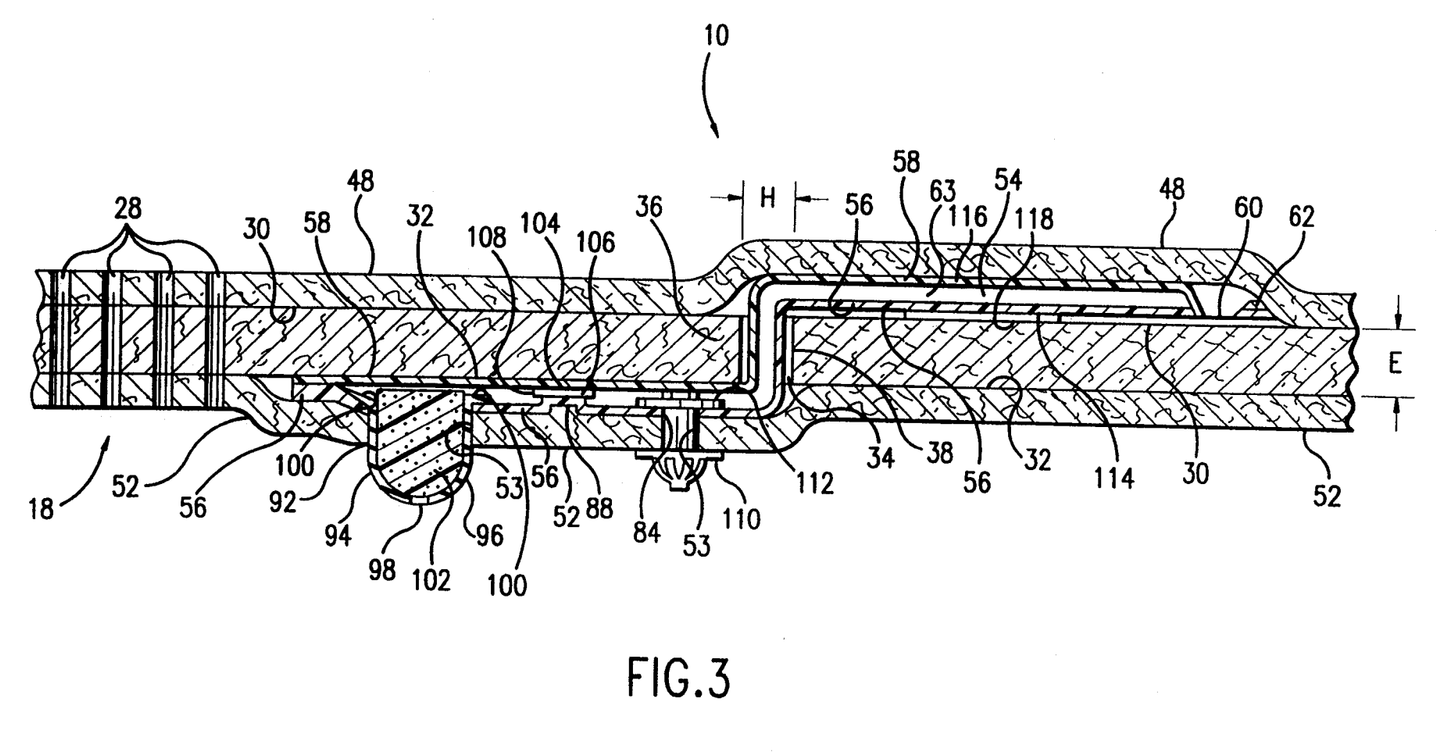
FIG. 3 is a sectional view taken along line 3—3 of FIG. 2.

As best seen in FIG. 3, belt 12 has a first surface 30 and a second surface 32 defining a thickness E of approximately ¼ inch. Belt 12 may be made from a variety of stiff yet resilient materials suitable for providing an adequate foundation for support including plastic and leather. In the preferred embodiment, belt 12 is made from relatively stiff leather. An aperture 34 extends completely through belt 12 in central portion 44, from first surface 30 to second surface 32. Aperture 34 is generally rectangular shaped and has opposing edges 36 and 38, and 40 and 42, respectively (best seen in FIGS. 1 and 2). Length G of edges 36 and 38, in the preferred embodiment, is approximately ⅜ inch. Length H of edges 40 and 42, in the preferred embodiment, is approximately ½ inch. Bladder 54 extends through aperture 34 in the manner described below.

Belt 12 is also provided with an outer covering 52 and an inner liner 48 which protect surfaces 30 and 32 of belt 12 and bladder 54 from damage. Outer covering 52 and inner liner 48 may be made of any durable material such as fabric, plastic, or leather and may be attached to belt 12 by any suitable means such as stitching 50. In the preferred embodiment, suede leather is utilized for both outer covering 52 and inner liner 48. Outer covering 52 also has the advantage that it may carry decorative or product identification stitching or embossing.

With continuing reference to the Figures, bladder 54 will now be described. Generally elongated in shape, bladder 54 is sized to substantially cover the user's lower back when support 10 is worn.

Figure 4:
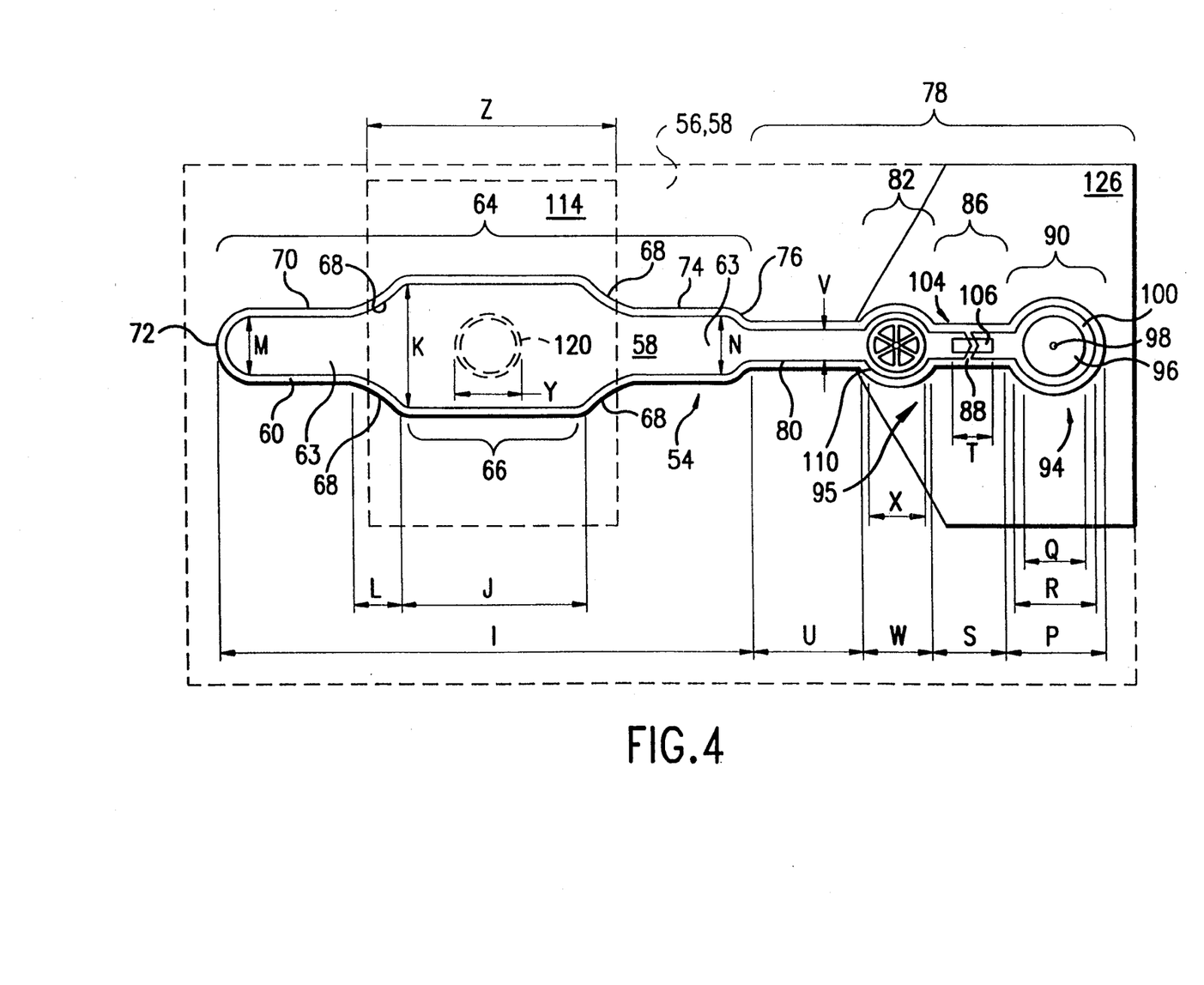
FIG. 4 is a plan view of the bladder assembly of the article of manufacture according to the present invention.

Bladder 54 is defined by a first rectangular sheet 56 and a second rectangular sheet 58 joined along a weld 60 to form a single inflatable chamber 63. First and second sheets 56 and 58 are preferably made of thermoplastic material such as a polyvinyl chloride or a polyurethane polymer. Weld 60 may be formed by using conventional heat sealing, radio frequency (RF) energy, or other sealing method to bond first and second sheets 56 and 58 together. After sheets 56 and 58 are welded, excess material outside the perimeter of bladder 54 may be trimmed as desired to allow unobstructed expansion of chamber 63.

Chamber 63 has an oblong portion shown generally at 64 and an elongated portion shown generally at 78. Oblong portion 64 provides general support to the lumbar spinal region of the wearer when support 10 is worn. Oblong portion 64 has a central portion 66, and first and second wings 70 and 74, respectively. In the preferred embodiment, oblong portion 64 has an overall length I of approximately 9 inches.

Central portion 66 of bladder 54 is dimensionally designed to specifically provide support to the vertebrae comprising the lumbar spinal region when support 10 is worn. The length of central portion 66 is designated by J which, in the preferred embodiment, is approximately 2 inches; the width K of central portion 66 is approximately 3 inches.

First and second wings 70 and 74 are disposed on each side of central portion 66 and provide support to the muscles immediately adjacent the spine when in their inflated condition. First and second wings 70 and 74 have tapered portions 68 having a length 5 which provide a transition between width K of central portion 66 and rounded end 72 of first wing 70 and rounded end 76 of second wing 74. Length L of tapered portions 68 is approximately 3½ inches. The diameter M of rounded end 72 in the preferred embodiment is approximately 1½ inches. Similarly, in the preferred embodiment, the end width N of rounded end 76 of second wing 74 is approximately 1½ inches.

Elongated portion 78 of bladder 54 is provided with inflation/deflation mechanism 95, which comprises a digital pump shown generally at 94, a one-way valve shown generally at 104 and an exhaust valve 110 which together function to inflate and deflate chamber 63.

Digital pump 94 comprises a dome-like cover 96 defining a circular aperture 98 therethrough, and a circular flange 100 extending from cover 96. A sponge 102 is disposed under cover 96 to maintain the domed shape of cover 96. Digital pump 94 is permanently joined to first sheet 56 through an aperture 92 formed therein. Cover 96 extends through aperture 92 until flange 100 abuts the interior surface of sheet 56. Flange 100 of digital pump 94 is then sealingly joined to first sheet 56 by using any conventional method such as heat-sealing so that digital pump 94 is integral with bladder 54 and unattached to second sheet 58.

To allow the wearer to directly depress digital pump 94, a corresponding aperture 53 is provided in outer covering 52. The domed portion of cover 96 extends through aperture 53. The manner in which digital pump 94 is affixed to a bladder and the operation of digital pump 94 is more fully set forth in U.S. Pat. No. 5,144,708 to Pekar, the disclosure of which is hereby incorporated in its entirety by reference.

In the preferred embodiment, the diameter of end portion 90, shown generally at P, is approximately 1¼ inches. The diameter of digital pump 94, shown generally at Q, is approximately 1 inch. The diameter of flange 100, shown generally at R, is approximately 1⅛ inches.

One-way valve 104 is disposed between digital pump 94 and chamber 63 in the intermediate portion 86 of bladder 54. One-way valve 104 is made from a thin tubular film 106, preferably plastic, having a central aperture 108 for allowing fluid to pass from digital pump 94 to chamber 63. A chevron-shaped weld 88 is disposed over first sheet 56, second sheet 58 and one-way valve 104 in the manner described in U.S. Pat. No. 5,144,708, discussed above. As a result, air is permitted to pass from digital pump 94 toward chamber 63, but blocked from passing in the reverse direction by one-way valve 104. In the preferred embodiment, the length of intermediate portion 86, shown generally at S, is approximately ¾ inch; length of one-way valve 104, shown generally at T, is approximately ⅞ inch.

Exhaust valve 110 exhausts fluid from chamber 63 to the atmosphere. Exhaust valve 110 is accommodated on expanded portion 82 of bladder 54 between chamber 63 and one-way valve 104. Exhaust valve 110 is permanently joined to first sheet 56 in the same manner as digital pump 94. Specifically, first sheet 56 defines an aperture 84 through which exhaust valve 110 extends so that flange 112 of exhaust valve 110 may be sealingly joined to first sheet 56 using any conventional method such as heat sealing. Exhaust valve 110 is therefore integral with bladder 54 and unattached to sheet 58. This arrangement allows exhaust valve 110 to fluidly communicate with chamber 63. To permit the wearer to manipulate exhaust valve 110, aperture 53 corresponding to the location of exhaust valve 110 is provided in outer covering 52. In the preferred embodiment, diameter W of expanded portion 82 is approximately ⅞ inch and diameter X of exhaust valve 110 is approximately ⅝ inch.

An example of a suitable exhaust valve 110 is described in pending U.S. patent application Ser. No. 07/973,670 filed Nov. 9, 1992, the disclosure of which is also hereby incorporated in its entirety by reference. The exhaust valve therein is designed to accept a hand-held inflator, which contains compressed gas. (Such an inflator is described in U.S. patent application Ser. No. 07/828,440 filed Jan. 31, 1992, the disclosure of which is hereby incorporated in its entirety by reference.) Compressed gas exits the inflator and enters the bladder through a one-way valve. Gas pressure may be relieved from bladder 54 by digitally depressing the exhaust valve. Therefore, exhaust valve 110 can be used both to inflate and deflate bladder 54. As a result, in an alternative embodiment, the use of exhaust valve 110 with the inflator allows digital pump 94, one-way valve 104, and associated bladder portions 86 and 90 to be eliminated from belt 12, which minimizes the parts necessary to inflate and deflate the bladder and reduces the overall weight and manufacturing cost of support 10. The disadvantage of this method is that the inflator is a separate container that is not fixed to the belt and must be carried separately.

It is desirable to leave chamber 63 disposed on the interior of belt 12 so that it is in direct contact with the user and to have inflation/deflation mechanism 95 disposed on the exterior of belt 12 so that it is accessible to the user when support 10 is worn. Therefore, when assembled, chamber 63 is disposed on first surface 30 of belt 12, while elongated portion 78 of bladder 54 is disposed on second surface 32 of belt 12. As a result, a transitional portion 80 of elongated portion 78 of bladder 54 extends through aperture 34 of belt 12 in an "S" type configuration (best seen in FIG. 3). Length U of transitional portion 80 must be sufficiently long enough to permit extension through belt aperture 34 without pinching; yet be narrow enough to prevent folding. In the preferred embodiment, length U is approximately 2⅞ inches; rectangular width V measures approximately ¼ inch wide.

Because intermediate portion 80 of bladder 54 is integral with second wing 74 of chamber 63 and with inflation/deflation mechanism 95, the provision of a separate conduit for communicating fluid between inflation/deflation mechanism 95 and chamber 63, as in the prior art, is avoided. This eliminates the additional manufacturing step and associated costs of joining a conduit to the bladder while minimizing the propensity for fluid leakage.

In use, a user inflates chamber 63 by depressing digital pump 94, which forces air from digital pump 94 through one-way valve 104 and elongated portion 78, and into chamber 63. In order to relieve pressure from chamber 63, the user simply depresses exhaust valve 110 which releases air from chamber 63 through exhaust valve 110 to the atmosphere.

Bladder 54 may be attached to belt 12 using conventional methods such as gluing. Because of the "S" type configuration of bladder 54 through belt aperture 34, oblong portion 64 and elongated portion 78 must be separately attached to opposite sides of belt 12. In the preferred embodiment, a connection tab 114 shown in FIG. 2 (shown in phantom in FIG. 4 to avoid obstructing the view of bladder 54) is fixed to second sheet 58 of bladder 54 by a circular weld 120. The side of connection tab 114 facing second sheet 58 is coated with a thermoplastic material to facilitate welding. Connection tab 114 may be made of any suitable material exhibiting characteristics which facilitate the application of a thermoplastic coating, glue, and stitching. In the preferred embodiment, connection tab 114 is made from a nylon-type material and is square in shape, having an edge length Z of approximately 4⅞ inches. Circular weld 120 has a diameter of approximately 1¼ inches, shown generally at Y. To facilitate welding connection tab 114 only to second sheet 8 and not to first sheet 56, a barrier layer (not shown) or release coating is disposed between first sheet 56 and second sheet 58 in the area of circular weld 120 prior to welding. The barrier layer prevents first sheet 56, second sheet 58, and connection tab 114 from all being welded together, thereby allowing chamber 63 to fully expand in response to fluid pressure. The barrier layer and methods of applying it are more fully described in U.S. Pat. No. 5,022,109 to Pekar discussed above.

Stitching, shown generally at 124, is used to attach connection tab 114 to first surface 30 of belt 12, thereby fixing chamber 63 to belt 12. Stitching 124 may simultaneously attach inner liner 48 to belt 12, thereby avoiding duplicative stitching operations. To enhance attachment, connection tab 114 and second sheet 56 may also be glued directly to first surface 30 of belt 12. By attaching only one side of bladder 54 to belt 12, chamber 63 is allowed to fully inflate and extend and bulge to provide maximum support to the wearer.

To attach elongated portion 78 to belt 12, waste material from first and second sheets 56 and 58 are left uncut from bladder 54 and form a second connection tab 126. Second connection tab 126 is glued and stitched 50 to second surface 32 of belt 12 in the same manner as connection tab 114. In an alternative embodiment, bladder 54 may be fixed to belt 12 by other permanent and semipermanent means such as a hook-and-pile fastener.

To use support 10, the user wraps belt 12 around the waist and buckles ends 16 and 18 together so that bladder 54 is placed in contact with the lower back. Once belt 12 is secured, the user manually depresses digital pump 94, forcing air through one-way valve 104 into chamber 63. The air pressure developed in chamber 63 determines, in part, the amount of support and comfort experienced by the user. Thus, the user may increase the amount of support provided by chamber 63 by performing additional depressions of digital pump 94. Alternatively, the user may decrease the amount of support by releasing air mass through exhaust valve 110. The amount of support exerted by chamber 63 may be adjusted according to individual need to obtain optimal support or comfort. In addition, the amount of air in chamber 63 can be readjusted as the user moves or changes activities, and as air pressure is lost through diffusion.

While the foregoing description of the preferred embodiment of the invention is specifically directed toward weight lifting belts, it is anticipated that the invention could be adapted for use in various other types of equipment other than those specifically mentioned. For example, the principles of the present invention could be translated into helmets for use in cycling and football and use in body protection pads for soccer and the like.

The foregoing description of the preferred embodiments of the invention have been presented for the purposes of illustration and description. It is not intended to be exhaustive or to limit the invention to the precise form disclosed, and obviously many possible modifications and variations are possible in light of the above teaching. For example, the dimensions of support 10 may be varied to accommodate different sizes as well as enlarged to support a spinal region greater than the lumbar region. In addition, various elements such as the liner and covering may be omitted.

The embodiments were chosen and described in order to best explain the principles of the present invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An article of manufacture, comprising:
   a rigid support having a first side and a second side defining an aperture located at a first position within said support which extends between said first side and said second side;
   a bladder disposed on said first side of said support having a portion which extends from said first side of said support through said aperture to said second side of said support; and
   an inflation mechanism positioned on said portion of said bladder disposed on and supported by said second side of said support at a second position different from said first position of said aperture;
   wherein said inflation mechanism is supported by a surface of said second side of said rigid support during inflation of said bladder.

2. An article according to claim 1, wherein said bladder comprises two laminated sheets of polyurethane.

3. An article according to claim 2, wherein said inflation mechanism is integrally formed with said bladder.

4. An article according to claim 3, wherein a portion of said inflation mechanism is attached to one of said laminated polyurethane sheets.

5. An article according to claim 4, wherein said inflation mechanism comprises a manual pump.

6. An article according to claim 1, further comprising:
   an exhaust valve in fluid communication with said bladder, said exhaust being integrally formed with said bladder.

7. An article according to claim 1, wherein said portion of said bladder which extends from said first side of said support through said aperture to said second side of said support is elongated.

8. An article according to claim 7 wherein said inflation mechanism is disposed on said elongated portion of said bladder.

9. An article according to claim 8, wherein a portion of said bladder is oblong-shaped.

10. An article according to claim 9, wherein said oblong-shaped portion of said bladder is disposed on said first side of said support.

11. An article according to claim 10, wherein said elongated portion of said bladder extends through said aperture to said second side of said support.

12. An article according to claim 9, wherein said bladder comprises a single chamber.

13. An article according to claim 12 further comprising:
   a connection tab for affixing said oblong-shaped portion of said bladder to said first side of said support.

14. An article according to claim 1, wherein said support comprises a belt.

15. An inflatable back support, comprising:
   a rigid support adapted to be worn about the waist of a user, said rigid support having a first side and a second side, a portion of said first side being in a facing relationship with the user's back when said rigid support is worn about the user's waist;
   an aperture defined by said rigid support which extends between said first side and said second side of said support;
   an inflatable bladder for applying pressure to the back of the user, said bladder having a first portion disposed on said first side of said support and a second portion which extends from said first side of said support through said aperture to said second side of said support; and
   an inflation mechanism positioned on said second portion of said bladder disposed on and supported by said second side of said support at a location different from said location of said aperture;
   wherein said inflation mechanism is supported by a surface of said second side of said rigid support during inflation of said bladder.

16. The inflatable back support of claim 15, wherein said first portion of said bladder disposed on said first side of said support is oblong-shaped to provide support to the lumbar spinal region of the wearer's back when said bladder is in the inflated condition.

17. The inflatable back support of claim 16, wherein said second portion of said bladder which extends from said first side of said support through said aperture to said second side of said support is elongated.

18. The inflatable back support of claim 17, wherein said inflation mechanism is disposed on said elongated portion of said bladder.

19. The inflatable back support of claim 15, wherein said bladder comprises a single chamber.

20. The inflatable back support of claim 15 further comprising an exhaust valve disposed between said inflation mechanism and said first portion of said bladder.

* * * * *

UNITED STATES PATENT AND TRADEMARK OFFICE
CERTIFICATE OF CORRECTION

PATENT NO. : 5,437,615
DATED : August 1, 1995
INVENTOR(S) : Pekar, et. al.

It is certified that error appears in the above-identified patent and that said Letters Patent is hereby corrected as shown below:

Column 9, claim 6, after "exhaust, "insert --valve--.

Signed and Sealed this

Twenty-eighth Day of November 1995

Attest:

BRUCE LEHMAN

*Attesting Officer*   *Commissioner of Patents and Trademarks*